United States Patent [19]

Yasuda et al.

[11] 4,297,279
[45] Oct. 27, 1981

[54] IMIDAZOLEDICARBOXYLIC ACID DERIVATIVE

[75] Inventors: Naohiko Yasuda, Yokosuka; Eiji Nakanishi, Kawasaki, both of Japan

[73] Assignee: Ajinomoto Co., Inc., Tokyo, Japan

[21] Appl. No.: 134,681

[22] Filed: Mar. 27, 1980

[30] Foreign Application Priority Data

Mar. 27, 1979 [JP] Japan .................................. 54-36133

[51] Int. Cl.³ .................. C07D 499/04; C07D 501/02; C07D 487/04
[52] U.S. Cl. ................................. 260/239.1; 424/246; 424/271; 544/22; 544/25; 544/27; 544/28; 544/346
[58] Field of Search ........................ 544/22, 25, 27, 28, 544/346; 260/239.1

[56] References Cited

U.S. PATENT DOCUMENTS 4,101,661 7/1978 Kaltenbronn et al. ............... 544/27
4,156,724 5/1979 Yamada et al. ...................... 544/28
4,183,742 1/1980 Sasse et al. .......................... 544/346

4,217,450 8/1980 Yasuda et al. ....................... 544/25

Primary Examiner—Robert Gerstl
Assistant Examiner—Vera C. Clarke
Attorney, Agent, or Firm—Oblon, Fisher, Spivak, McClelland & Maier

[57] ABSTRACT

A reactive derivative of imidazolecarboxylic acid having the formula:

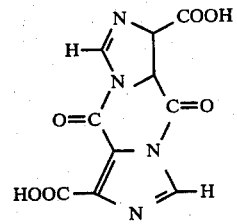

is useful in preparing imidazoledicarboxylic acid derivatives of alpha-aminopenicillins and cephalosporins.

5 Claims, No Drawings

IMIDAZOLEDICARBOXYLIC ACID DERIVATIVE

BACKGROUND OF THE INVENTION

1. Field of the Invention

This invention relates to novel derivatives of imidazoledicarboxylic acids and more particularly to such derivatives which are useful in preparing modified penicillins and cephalosporins. The invention also relates to a process for producing modified penicillins and cephalosporins and the like using the novel reactive derivatives of imidazoledicarboxylic acids.

2. Description of the Prior Art

Among the penicillins and cephalosporins which are useful antibiotics are those which contain an amino acid substituent at the 6(7)-amino group. These may be represented by the formula:

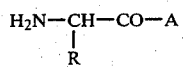

wherein A is an organic radical selected from the group consisting of:

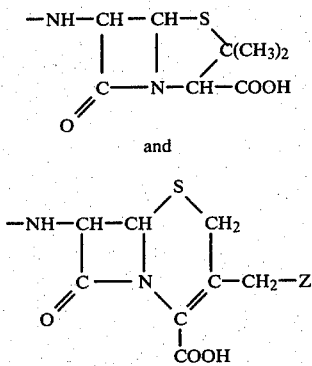

Z is selected from the group consisting of hydrogen, acyloxy such as acetoxy, carbamoyloxy, heteroaromatic thio such as 5-(1-methyltetrazolyl)thio and quaternary ammonium such as substituted or unsubstituted pyridinium, quinolinium or picolinium.

These aminopenicillins and cephalosporins are prepared by coupling an alpha-amino acid to the amine group in the 6(7)-position. Amino acids used for preparing such alpha-aminopenicillins and cephalosporins include phenylglycine, (4-hydroxyphenyl)glycine, and the like. These amino acids may be of the L-, D-, or DL-configuration. In many cases, the D-configuration has superior antibacterial activity.

It is known that the antibacterial activity of penicillins and cephalosporins of this type can be increased by further modification of the molecule with an imidazoledicarboxylic acid to produce an antibiotic having the following formula:

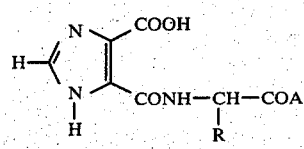

wherein R and A have the signification defined above. Antibiotics of this formula are disclosed in Japanese Published patent application No. 5974/1979 (German Offenlegungsschrift No. 28 26 546). These antibiotics have superior antibacterial activity especially against *Pseudomonas aeruginosa*, as compared with the unmodified penicillins and cephalosporins.

These improved antibiotics can be prepared by preparing a reactive derivative of an imidazoledicarboxylic acid of the formula:

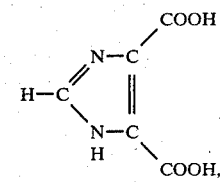

for example, the acid chloride thereof, and condensing this reactive derivative with alpha-aminopenicillins or cephalosporins having the general formula:

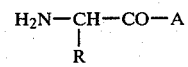

wherein A and R are as defined above. However, when the condensation reaction is carried out using known reactive derivatives of the imidazoledicarboxylic acid such as the acid chloride derivative, the process has a number of drawbacks. It has been found that more than 2 moles of the acid chloride is needed per 1 mole of aminopenicillin or cephalosporin, many side reactions are encountered and the yield is low. For example, in the process disclosed in Japanese Published patent application No. 5974/1979, which uses the acid chloride derivative of the imidazoledicarboxylic acid, the yield ranges from 10 to 40%.

Hence, a need has continued to exist for an improved method for preparing alpha-amino penicillins and cephalosporins modified with imidazole dicarboxylic acids.

SUMMARY OF THE INVENTION

Hence, it is an object of this invention to provide an improved reactive derivative of an imidazoledicarboxylic acid suitable for preparing modified alpha-aminopenicillins and cephalosporins.

A further object is to provide an improved process for preparing modified alpha-aminopenicillins and cephalosporins by reacting the alpha-aminopenicillins and cephalosporins with an improved reactive derivative of an imidazoledicarboxylic acid.

Further objects of the invention will be apparent from the description which follows.

The objects of the invention are accomplished by preparing an improved reactive derivative of an imidazoledicarboxylic acid having the formula:

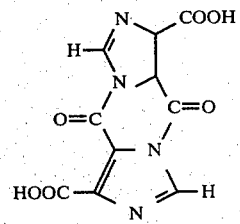

The compound of this invention reacts readily with amines represented by the formula H₂N—R', where R' represents an organic radical, and therefore is very useful as a reagent for preparing imidazoledicarboxylic acid monoamides of the formula

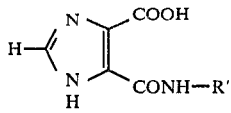

The reactive derivative of this invention therefore may be used to prepare modified alpha-aminopenicillins and cephalosporins by reaction with the unmodified compounds which have a free amino group, in solution in a suitable solvent in the presence of a base.

DETAILED DESCRIPTION OF THE PREFERRED EMBODIMENTS

The reactive derivative of imidazoledicarboxylic acid of this invention may be prepared by hydrolyzing a compound of the formula:

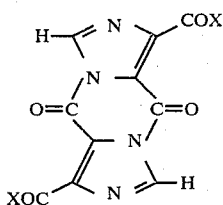

wherein X is a halogen.

In a preferred method of synthesizing the compound of this invention, 1H-imidazole-4,5-dicarboxylic acid is reacted with thionyl chloride under conditions in which the chlorination and condensation take place simultaneously to yield 5,10-dioxo-5,10-dihydroimidazo[1,5-a:1',5'-d]pyrazinedicarboxylic acid dichloride which is subsequently hydrolyzed to yield the compound of this invention. The hydrolysis may be accomplished by stirring the diacid dichloride with water at 10°–20° C. until the hydrolysis is complete. Thus, the synthesis of the compound of this invention by the preferred method may be illustrated by the following reaction scheme:

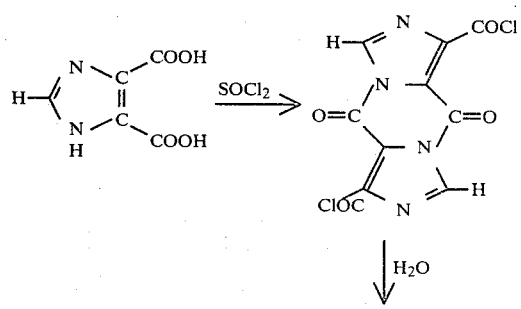

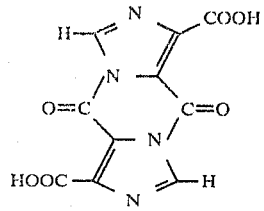

In preparing modified alpha-aminopenicillins or cephalosporins using the novel reactive derivative of an imidazoledicarboxylic acid of this invention, the penicillins or cephalosporins to be modified are dissolved in a suitable solvent in the presence of a base such as an alkali metal carbonate, an alkali metal bicarbonate, a trialkylamine, pyridine, or the like, and the compound of this invention is added to the solution. Suitable solvents include water, acetone, dioxane, acetonitrile, chloroform, dichloromethane, tetrahydrofuran (THF), dimethylformamide (DMF) and the like. Mixtures of hydrophilic organic solvents with water may also be used. The reaction may be conducted at a temperature in the range from 0° to 40° C. Preferably, 2 moles of alpha-aminopenicillin or cephalosporin are used for each mole of the compound of this invention.

In the modification reaction, α-aminopenicillins or cephalosporins in which the carboxyl group on the ring is esterified can be used. For example, t-butyl esters, benzyl esters, silyl esters, trichloroethyl esters, diphenylmethyl esters, and the like, can be used in the reaction. Subsequent to the modification reaction, the ester groups can be removed to regenerate the free carboxylic acid groups.

Modified alpha-aminocephalosporins wherein Z is a heteroaromatic thio group or tertiary ammonium group can be obtained by synthesizing the corresponding cephalosporins wherein Z is an acetoxy group and then replacing the acetoxy group by the heteroaromatic thio group or quaternary ammonium group.

The reaction products of the modification reaction can be isolated in pure form by known procedures, for example by extraction, column chromatography, recrystallization, and the like.

Having generally described the invention, a more complete understanding can be obtained by reference to certain specific examples, which are provided for purposes of illustration only and are not intended to be limiting unless otherwise specified.

EXAMPLE 1

This example illustrates the synthesis of the novel compound of this invention.

Imidazoledicarboxylic acid (7.8 g, 0.05 M) was suspended in dry benzene (100 ml), and thereto DMF (4 ml) and then thionyl chloride (30 ml) were added. The thus obtained mixture was refluxed at a temperature of 85° C. while stirring. After completion of the reaction, the reaction mixture was concentrated to yield solid material. To the thus obtained material, dry benzene (50 ml) was added and the mixture was concentrated to yield solid material, once more. To the remaining material benzene (50 ml) was added and the mixture was stirred at room temperature for 30 minutes. Insoluble solid material was collected by filtration and then washed with benzene and dried under reduced pressure to give the desired product, 5,10-dioxo-5, 10-dihydrodiimidazo [1,5a:1',5'-d]pyrazine-1,6-dicarboxylic acid dichloride (7.0 g, yield: 89%).

Elemental analysis:
Found: C 38.03%, H 0.74%, N 17.81%, Cl 22.37%, Calcd. as $C_{10}H_2N_4O_4Cl_2$, C 38.36%, H 0.64%, N 17.90%, Cl 22.65%.

The thus obtained acid chloride (7.0 g) was suspended in water (150 ml) and the mixture was stirred at 10°–20° C. overnight. An insoluble solid material was obtained by filtration and washed with water, a small amount of THF, and then ether. The material was dried under reduced pressure to give the desired product, 5,10-dioxo-5,10-dihydrodiimidazo [1,5a:1',5'-d]pyrazine-1,6-dicarboxylic acid dihydrate (7.0 g, yield: 100%).

M.P., 284° C. (dec.)

I.R. spectrum: 3500 cm$^{-1}$, 1750 cm$^{-1}$, 1710 cm$^{-1}$, 1255 cm$^{-1}$, 930 cm$^{-1}$ Elemental analysis:
Found: C 38.65%, H 2.40%, N 18.02%, Calcd. as $C_{10}H_4N_4O_6 \cdot 2H_2O$, C 38.47%, H 2.58%, N 17.95%.

EXAMPLE 2

This example illustrates the use of the compound of this invention to prepare amide derivatives of imidazoledicarboxylic acid.

Benzylamine (1.2 g, 11 mM) was dissolved in dichloromethane (50 ml) and triethylamine (2.8 ml, 20 mM) was added thereto. To this mixture 5,10-dioxo-5,10-dihydrodiimidazo [1,5-a:1',5'-d]pyrazine-1,6-dicarboxylic acid dihydrate (1.1 g, 3.6 ml) was added and the mixture was stirred at 40° C. for 5 hours. To the reaction mixture ether (100 ml) was added and the precipitated crystalline material was collected by filtration. The thus obtained crystals were added to water (100 ml) and dissolved by adjusting the water solution to pH 7 with NaOH. The thus obtained solution was washed with ethyl acetate. The water phase was adjusted to pH 2 with 2 NHCl and the precipitated solid was obtained by filtration and dried. The crystalline material was dissolved in THF (250 ml) of 50° C. and an insoluble material was separated by filtration. The obtained mother liquor was concentrated and ether-petroleum ether added thereto to precipitate crystals. After overnight, the precipitated crystals were collected by filtration and washed with petroleum ether. These crystals were dried under reduced pressure to give the desired product, imidazole-4-N-benzylcarboxyamide-5-carboxylic acid (1.2 g, yield: 68%).

Elemental analysis:
Found: C 58.50%, H 4.51%, N 17.16%; Calcd. as $C_{12}H_{11}N_3O_3$, C 58.77%, H 4.52%, N 17.14%.

$^1$H-N.M.R. spectrum (solvent: DMSO-D$_2$O):

δ 4.58 (S, 2H) 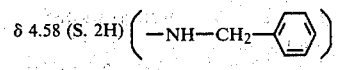

7.20 7.45 (m, 5H) 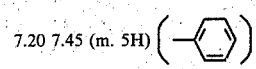

8.05 (S, 1H) (—H in the second position of imidazole group)

EXAMPLE 3

This example illustrates the modification of a number of penicillins and cephalosporins using the novel reagent of this invention.

For each compound modified the following procedure was used:

The compound to be modified (16 mM) was suspended in dry dichloromethane (100 ml) and triethylamine (6 ml) was added thereto. The mixture was stirred for 30 minutes while being cooled with ice-water. To this solution the compound of the present invention, i.e., 5,10-dioxo-5,10-dihydrodiimidazo-[1,5a:1',5'-d]pyrazine-1,6-dicarboxylic acid dihydrate (2.2 g, 7 mM) was added while stirring and cooling. The mixture was stirred overnight, and concentrated to give solid material. This material was added to water (50 ml) and stirred to give a homogeneous solution. The solution was adjusted to pH 8 with 6% aqueous HCl solution, stirred for 10 minutes, and then washed with ethyl acetate (50 ml). The water phase was adjusted to pH 2 with 6% aqueous HCl solution, and the mixture was stirred for 20 minutes. The precipitated crystalline material was collected by filtration, washed with water, and then dried under reduced pressure at 40° C. The thus obtained solid material was suspended in a solvent (500 ml) obtained by mixing ethylacetate and methanol (volume ratio: 1/1), and the mixture was stirred at 40° C. for 20 minutes. An insoluble material was separated by filtration. Thus obtained organic phase was concentrated under reduced pressure to volume of 50 ml, and ether (500 ml) was added thereto. This mixture was left overnight in the refrigerator. Thus precipitated crystals were collected, washed with petroleum ether and dried to give the desired product, For each compound a control experiment was run in which the compound was modified using the diacid dichloride, which is a known compound in order to illustrate the deficiencies of using the diacid dichloride for modifying alpha-aminopenicillins and cephalosporins. The following procedure was used:

The compound to be modified (100 mM) was suspended in dry dichloromethane (40 ml) and triethylamine (14 ml) was added thereto. The mixture was stirred for 30 minutes with cooling. In a separate vessel, the dichloride derivative (6.3 g, 20 mM) was suspended in dry dichloromethane (40 ml) and to this mixture dichloromethane solution of the compound to be modified, which had been previously synthesized, was added dropwise slowly over 15 minutes. After the completion of the reaction, the mixture was further stirred for 2 hours while being cooled with ice-water. Insoluble material was removed by filtration from the reaction solution and the thus obtained solution was concentrated under reduced pressure at 30° C. or lower to solid material. The thus obtained material was dissolved in water (70 ml) and then ethyl acetate (70 ml) was added thereto to make two phases. The ethyl acetate phase was removed and to the obtained aqueous phase ethyl acetate (100 ml) was added and then 6% aqueous HCl solution was added while stirring to adjust the aqueous phase to pH 2. The precipitated insoluble material was removed by filtration and a solution having two phases was obtained. From the aqueous phase, organic material was extracted with ethyl acetate (100 ml) once more. All the obtained ethyl acetate phases were combined and dried over magnesium sulfate. The ethyl acetate solution was concentrated at 30° C. or lower and to the thus obtained solid material ether (100 ml) was added to produce a powder. The powder was collected by filtration and dried to give the desired product.

The compounds used as starting materials, the products, and the yields using the compound of this invention and the dichloride derivative are presented in Table 1.

TABLE 1

| Example No. | Compound to be modified (Starting Material) | Product | Yield Compound of Present Invention | Dichloride Derivative |
|---|---|---|---|---|
| 3a | Anhydrous 7β-[D(−)-α-amino-phenylacet-amido] cephalos-poranic acid | 7β-[D(−)-α-(4-car-boxyimidazole-5-carboxamido)-phenylacetamido] cephalosporanic acid | 75% | 34% |
| 3b | Anhydrous D(−)-α aminobenzyl-penicillin | D-α-(4-carboxy-imidazole-5-car-boxamido)benzyl-penicillin | 74% | 12% |
| 3c | D(−)-α-amino-p-hydroxybenzyl-penicillin . 3H₂O | D-α-(4-carboxy-imidazole-5-carboxyamido)-p-hydroxybenzyl-penicillin . 1H₂O | 45% | 8% |
| 3d | Anhydrous 7-β-[D(−)-α-(4-car-(−)-α-amino-p-hydroxyphenyl-acetamido] cephalosporanic acid | boxyimidazole-5-carboxyamido)-p-hydroxyphenylacet-amido]cephalo-sporanic acid | | |

The physical properties of the compounds produced in Examples 3a–3d are as follows:

Example 3a: 7-β-[D(-)-α-(4-carboxyimidazole-5-carboxamido)phenylacetamido]cephalosporanic acid
Elemental analysis:
Found: C 49.66%, H 3.98%, N 12.77%, S 5.66%, Calcd. for $C_{23}H_{21}N_5O_9.1H_2O$, C 49.19%, H 4.14%, N 12.4%, S 5.71%.

| | |
|---|---|
| Thin Layer Chromatography (TLC) (silica gel) | $R_f = 0.70$ |
| I.R. spectrum (Nujol) | |
| $\nu$CO(β-lactum) | = 1775 cm$^{-1}$ |
| $\nu$(CO(—OCOCH₃) | = 1745 cm$^{-1}$ |
| N.M.R. spectrum of the disodium salt (Solvent:D₂O) | |
| ppm 2.13 (s, 3H) | (—OCOCH₃) |
| 3.36 (m, 2H) | (>CH₂, 2-position) |
| ppm 5.02 (d, 1H) | (—H, 6-position) |
| 5.73 (m, 2H) | (—H, 7-position) |
| 7.50 (bs, 5H) | (phenyl-CH—) |
| 7.80 (s, H) | (—H, 2-position of imidazole) |

Example 3b: D-α-(4-carboxyimidazole-5-carboxamido)benzylpenicillin
Elemental analysis:
Found: C 50.77%, H 4.51%, N 14.00%, S 6.35%, Calcd. for $C_{21}H_{21}N_5O_7S$, C 51.73%, H 4.35%, N 14.37%, S 6.58%.
Thin Layer Chromatography (TLC) (silica gel) $R_f = 0.45$
I.R. spectrum (Nujol)
$\nu$CO(β-lactam) = 1773 cm$^{-1}$
The thus obtained compound was converted to the disodium salt thereof by the following methods.
D-α-(4-carboxyimidazole-5-carboxamido)benzyl-penicillin (0.5 g, 1.0 mM) was dissolved in a mixture of methanol (15 ml) and ethyl acetate (10 ml) and to the solution thus obtained 2-ethylhexane carboxylic acid sodium salt n-butanol solution (2M/l) (1.23 ml) was added. The mixture was stirred for 10 minutes. Crystallized material was produced by adding ethyl acetate (150 ml) dropwise to the solution. Crystals were obtained by filtration and dried, and thereby D-α-(4-carboxyimidazole-5-carboxamido)benzylpenicillin disodium salt monohydroate [I] (0.35 g) was obtained.
Elemental analysis:
Found: C 46.67%, H 4.19%, N 12.32% calcd. for $C_{21}H_{19}N_5O_7SNa_2.1H_2O$, C 45.90%, H 3.86%, N 12.74%.

N.M.R. spectrum (D₂O, δ)

| | |
|---|---|
| ppm 1.50 (b.s. 6H) | (>C(CH₃)(CH₃), 2-position) |
| 4.30 (s, 1H) | (—H, 3-position) |
| 5.40–5.80 (m, 3H) | (—CH, —H 5- and 6- position) |
| 7.47 (b.s., 5H) | (phenyl) |
| 7.82 (s, 1H) | (—H, 2-position in imidazole) |

Example 3c: D-α-(4-carboximidazole-5-carboxamido)-p-hydroxybenzylpenicillin monohydrate
Elemental analysis:
Found: C 48.82%, H 4.50%, N 13.03%, Calcd. as $C_{21}H_{21}N_5SO_8.1H_2O$, C 48.35%, H 4.45%, N 13.43%.
I.R. spectrum (Nujol):
$\nu$C=O (β-lactam) = 1770 cm$^{-1}$
N.M.R. spectrum (Solvent: DMSO-D₂O):

| | |
|---|---|
| δ 1.42 (s., 3H) | (>C(CH₃)(CH₃)) |
| 1.56 (s., 3H) | |

| δ | 4.23 (s., 1H) | (—H in the 3-position) |
|---|---|---|
| | 5.37 (d., 1H) | (—H in the 5-position) |
| | 5.50 (d., 1H) | (—H in the 6-position) |
| | 5.70 (s., 1H) | —CH—<br>⏐<br>⌬<br>OH |
| | 6.75 (d., 2H)<br>7.30 (d., 2H) | (—⌬—OH) |
| | 8.06 (s., 1H) | (—H in the 2-position of imidazole group) |

Example 3d: 7-β-[D(—)-α-(4-carboxyimidazole-5-carboxamido)-p-hydroxyphenylacetamido]cephalosporanic acid,
I.R. spectrum (Nujol):
$\nu$C=O (—lactam)=1775 cm$^{-1}$
$\nu$C=O (—OCOCH$_3$)=1730 cm$^{-1}$
N.M.R. spectrum (Solvent: DMSO-D$_2$O)

| δ | 2.03 (s., 3H) | (—OCOCH$_3$) |
|---|---|---|
| | 3.46 (m., 2H) | (=CH$_2$ in the 2-position) |
| | 4.82 (q., 2H) | (=CH$_2$ in the 3-position) |
| | 5.03 (d., 1H) | (—H in the 6-position) |
| | 5.70 (s., 1H) | (—CH—<br>⏐<br>⌬<br>OH) |
| | 5.76 (d., 1H) | (—H in the 7-position) |
| | 6.80 (d., 2H)<br>7.36 (d., 2H) | (—⌬—OH) |
| | 8.06 (s., 1H) | (—H in the 2-position of imidazole group) |

EXAMPLE 4

7-β-[D-(—)-α-(4-carboxyimidazole-5-carboxamido)-phenylacetamido]cephalosporanic acid.2Na salt (770 mg, 1.3 mM) as prepared in Example 3a, and converted to the 2Na salt in the same manner as the compound of Example 3b, and 1-methyl-5-mercapto-1H-tetrazole (150 mg, 1.3 mM) were dissolved in pH 6.4 phosphate buffer solution (10 ml). At this time, the solution was adjusted to pH 6.4 with 2N NaOH solution. This solution was reacted at 60° C. with stirring for 24 hours. Five hours after starting the reaction, the mixture was adjusted to pH 6.4 with 2N NaOH solution.

To the reaction mixture water (20 ml) was added and the solution was adjusted to pH 7. The aqueous solution was washed with ethyl acetate (30 ml). To the obtained aqueous layer ethyl acetate (50 ml) was added and 6% hydrochloric acid solution was added to adjust the aqueous layer to pH 2. An insoluble material was removed by filtration to yield a solution having 2 layers. The aqueous solution was extracted with ethyl acetate (50 ml), once more. The obtained ethyl acetate solutions were combined, washed with water and dried with anhydrous magnesium sulfate. The ethyl acetate solution was concentrated at a temperature lower than 30° C. and the residue was triturated with ether (50 ml). The triturated material was collected by filtration and dried to give the desired compound, 7-β-[D-(—)-α-(4-carboxyimidazole-5-carboxamido)phenylacetamido]-3-[[(1-methyl-1H-tetrazol-5-yl)thio]methyl]-3-cephem-4-carboxylic acid monohydrate (160 mg, yield: 27%).

The 2 Na salt of this compound was produced in the same manner as for the compound of Example 3b.
Elemental analysis:
Found C 43.01%, H 3.56%, Na 6.33%, Calcd. for C$_{23}$H$_{19}$N$_9$O$_7$S$_2$Na$_2$, C 41.81%, H 3.06%, Na 6.96%.

| TLC (silica gel) | | R$_f$ = 0.23 |
|---|---|---|
| I.R. spectrum (Nujol): | | |
| $\nu$C=O (β-lactam) = 1765 cm$^{-1}$ | | |
| N.M.R. spectrum (D$_2$O, δ) | | |
| ppm | 3.10–3.60 (m, 2H) | (CH$_2$, 2-position) |
| | 3.88 (s, 3H) | (—CH$_3$ in the tetrazole) |
| | 4.00–4.20 (m, 2H) | (—CH$_2$—S—, 3-position) |
| | 4.93 (d, 1H) | (—H 6-position) |
| | 5.31–5.67 (m, 2H) | (—H, 7-position; —CH—<br>⏐<br>⌬) |
| | 7.30 (bs, 5H) | (—⌬) |
| | 7.63 (s, 1H) | (—H, 2-position in imidazole) |

EXAMPLE 5

7-β-[D-(—)-α-(4-carboxyimidazole-5-carboxamido)-phenylacetamido]-cephalosporanic acid.2Na salt (1.17 g, 2mM) was dissolved in water (12 ml) and 4-pyridineethanesulfonic acid (0.75 g, 4 mM) was added thereto. The solution was adjusted to pH 7 with 2N NaOH solution. To this solution sodium iodide (8.3 g) was added and this solution was reacted at 70° C. with stirring for 2 hours. The reaction mixture was treated with Amberlite XAD-2 produced by Rohm & Haas Co. (700 ml) in a column. By elution with water the fractions having the desired compound were collected. The solution was lyophilized to give the desired compound, 7-β-[D-(—)-α-(4-carboxyimidazole-5-carboxamido)-phenylacetamido]-3-(4-α-sulphoethylpyridiniummethyl-3-cephem-4-carboxylic acid disodium salt trihydrate (0.2 g, yield: 14%).

Elemental analysis:
Found: C 43.26%, H 3.66%, N 10.61%, S 8.15%, Na 6.0%, Calcd. for C$_{28}$H$_{24}$N$_6$O$_{10}$S$_2$Na$_2$.3H$_2$O, C 43.74%, H 3.94%, N 10.93%, S 8.34%, Na 5.98%.
I.R. spectrum (Nujol)
$\nu$C=O (β-lactam)=1770 cm$^{-1}$
$\nu$SO$_2$(—SO$_3$H)=1220 cm$^{-1}$, 1045 cm$^{-1}$
N.M.R. spectrum (D$_2$O, δ).

| ppm | 3.10 (m, 2H) | (CH$_2$, 2-position) |
|---|---|---|
| | 3.36 (s, 4H) | (—CH$_2$CH$_2$SO$_3$H) |
| | 5.13 (d, 1H) | (—H, 6-position) |
| ppm | 5.35 (m, 2H) | (—CH$_2$—N⏝⏜, 3-position) |
| | 5.62 (s, 1H) | (—CH—<br>⏐<br>⌬) |
| | 5.77 (d, 1H)<br>7.50 (m, 5H) | (—H, 7-position)<br>(—⌬) |
| | 7.83 (s, 1H) | (—H, 2-position in imidazole) |

7.95 (d, 2H)
8.78 (d, 2H)   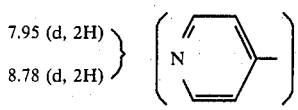

EXAMPLE 6

7-β-[D-(—)-α-(4-carboxyimidazole-5-carboxamido)-phenylacetamido]-cephalosporanic acid.2Na salt (1.17 g, 2 mM) was reacted with 3-pyridylacetic acid (0.55 g, 4 mM) to give 7-β-[D-(—)-α-(4-carboxyimidazole-5-carboxamido)phenylacetamido]-3-(3-carboxymethyl-pyridinium)methyl-2-cephem-4-carboxylic acid disodium salt (0.17 g, yield: 12%) in the same manner as in Example 5.

I.R. spectrum (Nujol)
νC=O (β-lactam)=1760 cm⁻¹
N.M.R. spectrum (D₂O, δ)

| ppm | | |
|---|---|---|
| 3.35 (m, 2H) | (>CH₂, 2-position) | |
| 3.60 (s, 2H) | (—N, CH₂CO₂) | |
| 4.80 (m, 2H) | (CH₂—N, 3-position) | |
| 5.10 (d, 1H) | (—H, 6-position) | |
| ppm 5.60 (s, 1H) | (—CH—) | |
| 5.73 (d, 1H) | (—H, 7-position) | |
| 7.45 (m, 5H) | | |
| 7.80 (s, 1H) | (—H, 2-position in imidazole) | |
| 7.90 & 8.40 (m, 4H) | (—N) | |

The imidazoledicarboxylic acid derivatives of alpha-aminopenicillins and cephalosporins prepared using the novel compound and process of this invention have a good antibacterial activity with a wide spectrum of activity, particularly against *Pseudomonas aeruginosa*.

Comparative Minimun Inhibitory Concentrations (MIC) (the minimum concentration of the compound in micrograms per milliliter required to inhibit the growth of the test organism in a culture) obtained using *Pseudomonas aeruginosa* AJ 2116 as the test organism, are presented in Table 2.

TABLE 2

| Example No. | MIC (μg/ml) |
|---|---|
| 3a | 50 |
| 3b | 12.5 |
| 3c | 12.5 |
| 3d | 50 |
| 4 | 50 |
| 5 | 12.5 |
| 6 | 12.5 |
| Carbenicillin | 100 |
| Ampicillin | More than 500 |

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A compound having the following formula:

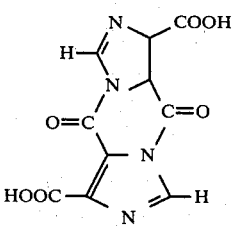

2. A process for producing a compound having the formula:

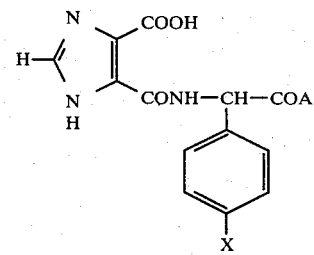

wherein A is an organic radical selected from the group consisting of

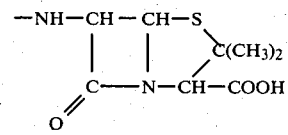

and

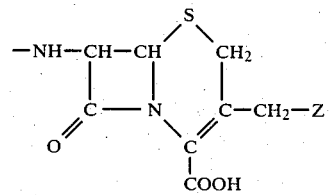

wherein Z is a radical selected from the group consisting of hydrogen, acyloxy, carbamoyloxy, heteroaromaticthio and quaternary ammonium, and X is a radical selected from the group consisting of hydrogen and hydroxyl, which comprises reacting an imidazoledicarboxylic acid derivative having the following formula:

with a compound having the following formula:

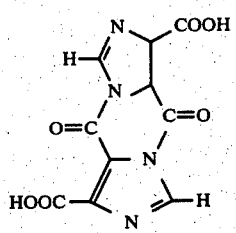

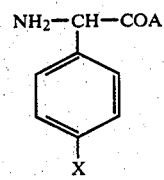

wherein A and X are as defined above.

3. The process of claim 2, wherein said reaction is conducted in a suitable solvent.

4. The process of claim 3, wherein said solvent is selected from the group consisting of water, acetone, dioxane, acetonitrile, chloroform, dichloromethane, tetrahydrofuran, and dimethylformamide.

5. The process of claim 2, wherein said reaction is conducted in a temperature range from 0° to 40° C.

* * * * *

UNITED STATES PATENT AND TRADEMARK OFFICE
CERTIFICATE OF CORRECTION

PATENT NO. : 4,297,279

DATED : October 27, 1981

INVENTOR(S) : NAOHIKO YASUDA ET AL

It is certified that error appears in the above—identified patent and that said Letters Patent is hereby corrected as shown below:

The Formula in the Abstract and the Formula at bottom of column 2 should read as follows:

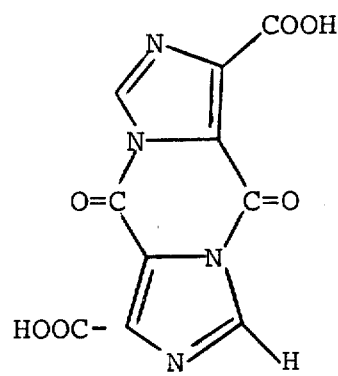

UNITED STATES PATENT AND TRADEMARK OFFICE
CERTIFICATE OF CORRECTION

PATENT NO. : 4,297,279
DATED : October 27, 1981
INVENTOR(S) : Naohiko Yasuda et al It is certified that error appears in the above—identified patent and that said Letters Patent is hereby corrected as shown below:

The Formula of Claim 1 should read as follows:

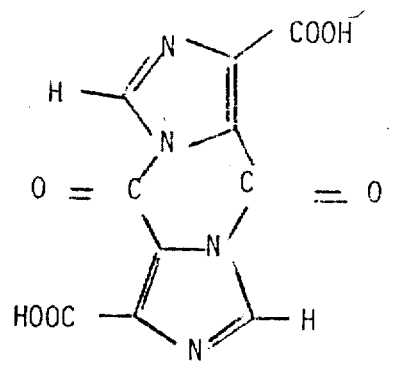

UNITED STATES PATENT AND TRADEMARK OFFICE
CERTIFICATE OF CORRECTION

PATENT NO. : 4,297,279
DATED : October 27, 1981
INVENTOR(S) : Naohiko Yasuda et al It is certified that error appears in the above—identified patent and that said Letters Patent is hereby corrected as shown below:

The first Formula of Claim 2 should read as follows:

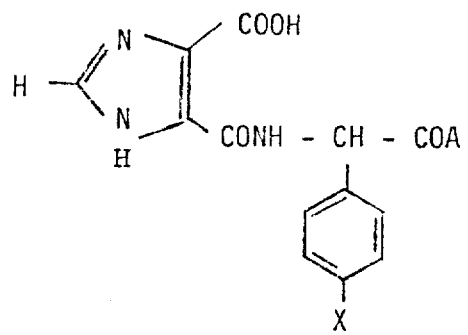

Signed and Sealed this

Eighteenth Day of May 1982

[SEAL]

Attest:

Attesting Officer

GERALD J. MOSSINGHOFF
Commissioner of Patents and Trademarks

UNITED STATES PATENT AND TRADEMARK OFFICE
CERTIFICATE OF CORRECTION

PATENT NO. : 4,297,279
DATED : October 27, 1981
INVENTOR(S) : NAOHIKO YASUDA ET AL It is certified that error appears in the above—identified patent and that said Letters Patent is hereby corrected as shown below:

The Formula in the Abstract and the Formula at bottom of column 2 should read as follows:

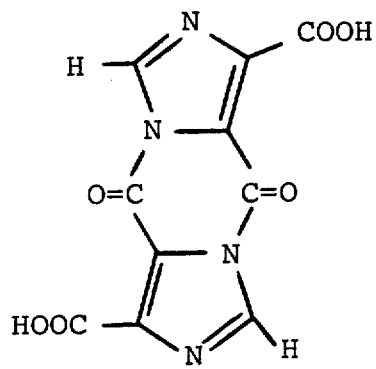

Signed and Sealed this

Seventh Day of September 1982

[SEAL]

Attest:

*Attesting Officer*

GERALD J. MOSSINGHOFF

*Commissioner of Patents and Trademarks*